United States Patent
Agarkar et al.

(10) Patent No.: US 10,752,586 B1
(45) Date of Patent: Aug. 25, 2020

(54) PROCESS FOR PREPARATION OF MOLINDONE

(71) Applicant: LUPIN LIMITED, Mumbai, Maharashtra (IN)

(72) Inventors: Amit Madanrao Agarkar, Maharashtra (IN); Tejas Vilas Puranik, Maharashtra (IN); Rajesh Bharat Gapat, Maharashtra (IN); Umesh Babanrao Rananaware, Maharashtra (IN); Radhakrishna Bhikaji Shivdavkar, Maharashtra (IN); Girij Pal Singh, Maharashtra (IN)

(73) Assignee: LUPIN LIMITED, Mumbai, Maharashtra (IN)

( * ) Notice: Subject to any disclaimer, the term of this patent is extended or adjusted under 35 U.S.C. 154(b) by 0 days.

(21) Appl. No.: 16/791,169

(22) Filed: Feb. 14, 2020

(30) Foreign Application Priority Data

Feb. 16, 2019 (IN) .............................. 201921006197
Nov. 11, 2019 (IN) .............................. 201921045847

(51) Int. Cl.
*C07D 209/08* (2006.01)
*C07C 49/403* (2006.01)

(52) U.S. Cl.
CPC .......... *C07D 209/08* (2013.01); *C07C 49/403* (2013.01)

(58) Field of Classification Search
CPC ............................ C07D 209/08; C07C 49/403
USPC .......................................................... 544/144
See application file for complete search history.

(56) References Cited

U.S. PATENT DOCUMENTS 3,491,093 A    1/1970  Pachter et al.

FOREIGN PATENT DOCUMENTS

WO    2014/042688 A1    3/2014

*Primary Examiner* — Kristin A Vajda
(74) *Attorney, Agent, or Firm* — Merchant & Gould P.C.

(57) ABSTRACT

The present invention provides process for preparation of molindone (I) comprising: a) reacting compound with cyclohexane-1,3-dione to form 2-(2-oxopentan-3-yl)cyclohexane-1,3-dione wherein X is Cl, Br or I, b) cyclizing 2-(2-oxopentan-3-yl)cyclohexane-1,3-dione to 2-methyl-3-ethyl-4-oxo-4,5,6,7-tetrahydroindole, c) reacting 2-methyl-3-ethyl-4-oxo-4,5,6,7-tetrahydroindole with morpholine and formaldehyde to give molindone (I), and d) optionally converting molindone (I) to its salt. The present invention further provides process for preparation of compound comprising: a) reacting compound with ethyl halide and another halide source to form compound wherein R is alkyl and X is Cl, Br or I; b) converting compound to compound.

11 Claims, No Drawings

PROCESS FOR PREPARATION OF MOLINDONE

This application claims the benefit of Serial No. 201921045841, filed Nov. 11, 2019 in India and Serial No. 201921006197, filed Feb. 16, 2019 in India, both of which are incorporated herein by reference. To the extent appropriate, a claim of priority is made to each of the above disclosed applications.

FIELD OF INVENTION

The present invention provides novel process for preparation of Molindone and its salts. The present invention also provides novel intermediate for preparation of Molindone.

BACKGROUND OF THE INVENTION

Molindone is chemically known as 4H-Indol-4-one, 3-ethyl-1,5,6,7-tetrahydro-2-methyl-5-(4-morpholinylmethyl) and represented by formula I. Molindone is indicated for management of schizophrenia and is under clinical trial for alternate therapies.

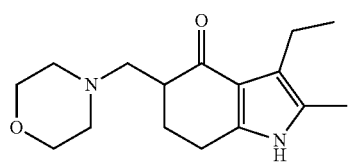
(I)

The compound molindone, process for its preparation and its pharmaceutically acceptable salts are disclosed in U.S. Pat. No. 3,491,093. Another application WO 2014042688 discloses methods of producing molindone. Since there are very limited methods for preparation of molindone reported in literature there exist a need for alternate process for preparation of molindone. The present invention provides novel process for preparation of Molindone (I) and its salts.

SUMMARY OF THE INVENTION

The present invention provides process for preparation of molindone (I) comprising:

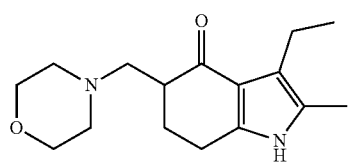
(I)

a) reacting compound (2) with cyclohexane-1,3-dione (3) to form 2-(2-oxopentan-3-yl)cyclohexane-1,3-dione (4)

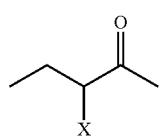
(2)

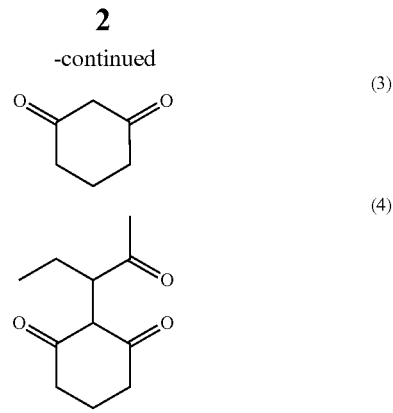

wherein X is Cl, Br or I,
b) cyclizing 2-(2-oxopentan-3-yl)cyclohexane-1,3-dione (4) to 2-methyl-3-ethyl-4-oxo-4,5,6,7-tetrahydroindole (5),

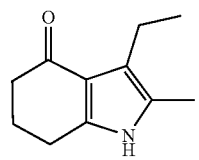
(5)

c) reacting 2-methyl-3-ethyl-4-oxo-4,5,6,7-tetrahydroindole (5) with morpholine and formaldehyde to give molindone (I), and
d) optionally converting molindone (I) to its salt.

The present invention further provides process for preparation of compound (2) comprising:
a) reacting compound (1') with ethyl halide and another halide source to form compound (2') wherein R is alkyl and X is Cl, Br or I

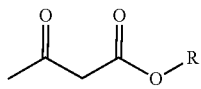
Compound (1')

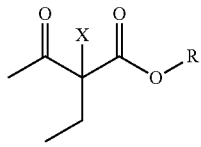
Compound (2')

b) converting compound (2') to compound (2).

DETAILED DESCRIPTION OF THE INVENTION

In the first embodiment, the present invention provides process for preparation of molindone (I) or its pharmaceutically salts thereof, comprising
a) reacting pentan-2-one (1) with a halide source to form compound (2), wherein X is Cl, Br or I
b) reacting compound (2) with cyclohexane-1,3-dione (3) to form 2-(2-oxopentan-3-yl)cyclohexane-1,3-dione (4),
c) cyclizing 2-(2-oxopentan-3-yl)cyclohexane-1,3-dione (4) to 2-methyl-3-ethyl-4-oxo-4,5,6,7-tetrahydroindole (5), d) reacting 2-methyl-3-ethyl-4-oxo-4,5,6,7-tetrahydroindole (5) with morpholine and formaldehyde to give molindone, and e) optionally converting molindone to its salt.

In the second embodiment, the present invention provides process for preparation of molindone (I) or its pharmaceutically salts thereof, comprising a) reacting compound (2) with cyclohexane-1,3-dione (3) to form 2-(2-oxopentan-3-yl)cyclohexane-1,3-dione (4), wherein X is Cl, Br or I, b) cyclizing 2-(2-oxopentan-3-yl)cyclohexane-1,3-dione (4) to 2-methyl-3-ethyl-4-oxo-4,5,6,7-tetrahydroindole (5), c) reacting 2-methyl-3-ethyl-4-oxo-4,5,6,7-tetrahydroindole (5) with morpholine and formaldehyde to give molindone, and d) optionally converting molindone to its salt.

In the third embodiment, the present invention provides novel compound 2-(2-oxopentan-3-yl)cyclohexane-1,3-dione (4). The compound (4) is useful as an intermediate for preparation of molindone. The compound (4) was isolated in a purity of above 95%. 2-(2-oxopentan-3-yl)cyclohexane-1,3-dione (4) is characterized by $^1$H NMR (500 MHz, CDCl$_3$), δ 5.14 (S 1H), δ 4.37 (d 1H), δ 2.50-2.55 (m 2H) δ 2.35-2.38 (m 2H), δ 2.16 (s 3H), δ 2.00-2.05 (m 2H) δ 1.88-1.90 (m 2H), δ 1.00-1.02 (m 3H); $^{13}$C NMR (500 MHz, CDCl$_3$), 206.04, 199.34, 176.63, 103.70, 77.12, 36.62, 28.88, 25.44, 21.00, 16.55, 9.41 ppm; Dept135 NMR (500 MHz, CDCl$_3$): 103.70, 83.78, 36.62, 28.87, 28.65, 25.45, 24.69, 21.00, 9.41 ppm; Mass: [M+1]=197.

In the fourth embodiment, the present invention provides process for preparation of 2-(2-oxopentan-3-yl)cyclohexane-1,3-dione (4), comprising a) reacting pentan-2-one (1) with a halide source to form compound (2), and wherein X is Cl Br or I b) reacting compound (2) with cyclohexane-1,3-dione (3) to form 2-(2-oxopentan-3-yl)cyclohexane-1,3-dione (4)

In the fifth embodiment, the present invention provides process for preparation of molindone (I) or its pharmaceutically salts thereof, comprising a) converting 2-(2-oxopentan-3-yl)cyclohexane-1,3-dione (4) to 2-methyl-3-ethyl-4-oxo-4,5,6,7-tetrahydroindole (5), b) reacting 2-methyl-3-ethyl-4-oxo-4,5,6,7-tetrahydroindole (5) with morpholine and formaldehyde to give molindone (I), and c) optionally converting molindone (I) to its salt.

In the sixth embodiment, the present invention provides process for preparation of 2-methyl-3-ethyl-4-oxo-4,5,6,7-tetrahydroindole (5) comprising reacting compound (2) with cyclohexane-1,3-dione (3) in presence of R—NH$_2$, base, solvent and catalyst, wherein R is H, alkyl or aryl.

In the seventh embodiment, the present invention provides process for preparation of molindone (I) or its pharmaceutically salts thereof, comprising a) reacting compound (2) with cyclohexane-1,3-dione (3) in presence of R—NH$_2$, base, solvent and catalyst, wherein R is H, alkyl or aryl to give 2-methyl-3-ethyl-4-oxo-4,5,6,7-tetrahydroindole (5) and b) reacting 2-methyl-3-ethyl-4-oxo-4,5,6,7-tetrahydroindole (5) with morpholine and formaldehyde to give molindone (I), and c) optionally converting molindone (I) to its salt.

In an eight embodiment, the present invention provides process for preparation of compound (2) comprising:

a) reacting compound (1') with ethyl halide and another halide source to form compound (2') wherein R is alkyl and X is Cl, Br or I b) converting compound (2') to compound (2)

In the present invention, the reaction of compound (1') with ethyl halide can be carried out in presence of base and a solvent. In the compound (1'), R is alkyl selected from straight chain or branched like methyl, ethyl, propyl, butyl and the like. In the reaction ethyl halide can be selected from ethyl iodide, ethyl bromide, ethyl chloride. The reaction can be carried out at a temperature of about 40 to 100° C. for 12 to 16 hours.

In the present invention, further reaction with another halide source can be carried out in presence of a solvent at a temperature of about 0 to 100° C. for 30 minutes to 6 hours. Another halide source can be selected from N-chlorosuccimide, N-bromosuccinimde, N-Iodosuccinimide, sulfuryl chloride and the like.

In the present invention, compound (2') is converted to compound (2) by treating compound (2') with acid in presence of water or aqueous solvent or a solvent. The acid can be selected from inorganic acid or organic acid. Inorganic acid may be selected from hydrochloric acid, sulfuric acid, and the like. Organic acid may be selected from acetic acid, para toluene sulfonic acid and the like. The reaction can be carried out at a temperature of about 20 to 100° C. for about 24 hours.

In the above reactions the solvent can be selected from organic polar or non-polar solvent. Polar solvent can be selected from alcohols like methanol, ethanol, butanol, propanol; nitriles like acetonitrile, propionitrile, butyronitrile; esters like ethyl acetate, ethyl acetoacetate, butyl acetate, propyl acetate; ketones like acetone, methyl ethyl ketone, methyl isobutyl ketone; ethers like tetrahydrofuran, dioxane, dimethoxyethane; dimethyl ether, diisopropyl ether, diethyl ether, methyl tert-butyl ether, 1,2-dimethbxy ethane, tetrahydrofuran, 1,4-dioxane; acids like acetic acid; other polar solvents like dimethylacetamide, dimethylformamide, dimethyl sulfoxide, water and mixtures thereof. Non-polar solvent can be selected from hydrocarbon solvent such as hexane, heptane, cyclohexane, petroleum ether, benzene, toluene, xylene and the like; chlorinated hydrocarbons like chloroform, dichloro methane, ethylene dichloride; or mixtures thereof.

The base can be selected from inorganic bases or organic base, the inorganic base can be selected from alkali metal carbonates such as sodium carbonate, potassium carbonate, lithium carbonate, cesium carbonate and the like; alkali metal bicarbonates such as sodium bicarbonate, potassium bicarbonate lithium bicarbonate, cesium bicarbonate and the like; alkali metal hydroxides such as sodium hydroxide, potassium hydroxide, lithium hydroxide and the like; alkali metal alkoxides such as sodium methoxide, sodium ethoxide, potassium methoxide, potassium ethoxide, sodium tert-.butoxide, potassium tert.butoxide, lithium tert.butoxide and the like; alkali metal hydrides such as sodium hydride, potassium hydride, lithium hydride and the like; alkali metal amides such as sodium amide, potassium amide, lithium amide and the like; ammonia; and the organic base can be selected from alkyl and aryl amines such as methylamine, ethylamine, dimethylamine, diethylamine, diisopropyl amine, diisopropylethylamine, diisobutylamine, triethylamine, tributylamine, tert.butyl amine, pyridine, 4-dimethylaminopyridine or mixtures thereof.

In the present invention, preparation of compound (2) can be carried out in stepwise manner, by isolation of the intermediates or can be carried out in-situ.

In the present invention, the reaction of pentan-2-one (1) with a halide source can be carried out in presence of a solvent. The solvent can be selected from organic polar or non-polar solvent. Polar solvent can be selected from alcohols like methanol, ethanol, butanol, propanol; nitriles like acetonitrile, propionitrile, butyronitrile; esters like ethyl acetate, ethyl acetoacetate, butyl acetate, propyl acetate; ketones like acetone, methyl ethyl ketone, methyl isobutyl ketone; ethers like tetrahydrofuran, dioxane, dimethoxyethane; dimethyl ether, diisopropyl ether, diethyl ether, methyl tert-butyl ether, 1,2-dimethbxy ethane, tetrahydrofuran, 1,4-dioxane; acids like acetic acid; other polar solvents like dimethylacetamide, dimethylformamide, dimethyl sulfoxide, water and mixtures thereof. Non-polar solvent can be selected from hydrocarbon solvent such as hexane, heptane, cyclohexane, petroleum ether, benzene, toluene, xylene and the like; chlorinated hydrocarbons like chloroform, dichloro methane, ethylene dichloride; or mixtures thereof. The halide source can be selected from N-chlorosuccimide, N-bromosuccinimde, N-Iodosuccinimide, sulfuryl chloride and the like. The reaction can be optionally carried out in presence of catalyst selected from sodium iodide, sodium bromide and the like. The compound (2) may be isolated by techniques known in art or may be used in-situ for further reactions. The reaction can be carried out at a temperature of 0-5° C. to reflux temperature of the solvent over a period 30 minutes to 24 hours.

The reaction of compound (2) with cyclohexane-1,3-dione (3) can be carried out in presence of a solvent and a base and optionally in presence of catalyst. The solvent can be selected from organic polar or non-polar solvent. Polar solvent can be selected from nitriles like acetonitrile, propionitrile, butyronitrile; esters like ethyl acetate, ethyl acetoacetate, butyl acetate, propyl acetate; ketones like acetone, methyl ethyl ketone, methyl isobutyl ketone; ethers like tetrahydrofuran, dioxane, dimethoxyethane, dimethyl ether, diisopropyl ether, diethyl ether, methyl tert-butyl ether, 1,2-dimethbxy ethane, tetrahydrofuran, 1,4-dioxane and the like; other polar solvents like dimethylacetamide, dimethylformamide, dimethyl sulfoxide, water and mixtures thereof. Non-polar solvent can be selected from hydrocarbon solvent such as hexane, heptane, cyclohexane, petroleum ether, benzene, toluene, xylene and the like; chlorinated hydrocarbons like chloroform, dichloro methane, ethylene dichloride; or mixtures thereof.

The base can be selected from inorganic bases or organic base, the inorganic base can be selected from alkali metal carbonates such as sodium carbonate, potassium carbonate, lithium carbonate, cesium carbonate and the like; alkali metal bicarbonates such as sodium bicarbonate, potassium bicarbonate lithium bicarbonate, cesium bicarbonate and the like; alkali metal hydroxides such as sodium hydroxide, potassium hydroxide, lithium hydroxide and the like; alkali metal alkoxides such as sodium methoxide, sodium ethoxide, potassium methoxide, potassium ethoxide, sodium tert-.butoxide, potassium tert.butoxide, lithium tert.butoxide and the like; alkali metal hydrides such as sodium hydride, potassium hydride, lithium hydride and the like; alkali metal amides such as sodium amide, potassium amide, lithium amide and the like; ammonia; and the organic base can be selected from alkyl and aryl amines such as methylamine, ethylamine, dimethylamine, diethylamine, diisopropyl amine, diisopropylethylamine, diisobutylamine, triethylamine, tributylamine, tert.butyl amine, pyridine, 4-dimethylaminopyridine or mixtures thereof.

The catalyst can be selected from quaternary ammonium salts, like tetra-n-butylammonium bromide, benzyltriethyl-ammonium chloride, methyltricaprylammonium chloride, methyltributylammonium chloride and the like. The reaction can be carried out at a temperature of 25-30° C. to reflux temperature of the solvent over a period 30 minutes to 24 hours. The product 2-(2-oxopentan-3-yl)cyclohexane-1,3-dione (4) can be isolated by techniques known in art or may be used in-situ for further reactions.

The cyclization of 2-(2-oxopentan-3-yl)cyclohexane-1,3-dione (4) to 2-methyl-3-ethyl-4-oxo-4,5,6,7-tetrahydroindole (5) can be carried out in presence of suitable reagent selected from urea/choline chloride, ammonium acetate, aqueous ammonia, methanolic ammonia, ammonium chloride or the like in presence of solvent. The solvent can be selected from organic polar or non-polar solvent, water or mixtures thereof. Polar solvent can be selected from alcohols like methanol, ethanol, butanol, propanol; esters like ethyl acetate, ethyl acetoacetate, butyl acetate, propyl acetate; ketones like acetone, methyl ethyl ketone, methyl isobutyl ketone; ether solvents such as ethers like tetrahydrofuran, dioxane, dimethoxyethane, dimethyl ether, diisopropyl ether, diethyl ether, methyl tert-butyl ether, 1,2-dimethbxy ethane, tetrahydrofuran, 1,4-dioxane and the like; nitrile solvents such as acetonitrile, propionitrile, isobutyronitrile and the like; acids like acetic acid and the like; other polar solvents like dimethylacetamide, dimethylformamide, dimethyl sulfoxide, water and mixtures thereof. Non-polar solvent can be selected from hydrocarbon solvent such as hexane, heptane, cyclohexane, petroleum ether, benzene, toluene, xylene and the like; chlorinated hydrocarbons like chloroform, dichloro methane, ethylene dichloride; or mixtures thereof. The product 2-methyl-3-ethyl-4-oxo-4,5,6,7-tetrahydroindole (5) can be isolated by techniques known in art.

The reaction of compound (2) with cyclohexane-1,3-dione (3) to give 2-methyl-3-ethyl-4-oxo-4,5,6,7-tetrahydroindole (5) can be carried out in presence of R—NH$_2$, base, solvent and catalyst, wherein R is H, alkyl or aryl.

The base is organic base selected from alkyl and aryl amines such as methylamine, ethylamine, dimethylamine, diethylamine, diisopropyl amine, diisopropylethylamine, diisobutylamine, triethylamine, tributylamine, tert.butyl amine, pyridine, 4-dimethylaminopyridine or mixtures thereof. The catalyst is preferably sulphonic acids on Wang resins, like Wang sulfonic acid and the like.

The solvent can be selected from organic polar, organic non-polar or water. Polar solvent can be selected from alcohols like methanol, ethanol, butanol, propanol; nitriles like acetonitrile, propionitrile, butyronitrile; esters like ethyl acetate, ethyl acetoacetate, butyl acetate, propyl acetate; ketones like acetone, methyl ethyl ketone, methyl isobutyl ketone; ethers like tetrahydrofuran, dioxane, dimethoxyethane; dimethyl ether, diisopropyl ether, diethyl ether, methyl tert-butyl ether, 1,2-dimethbxy ethane, tetrahydrofuran, 1,4-dioxane; acids like acetic acid; other polar solvents like dimethylacetamide, dimethylformamide, dimethyl sulfoxide, water and mixtures thereof. Non-polar solvent can be selected from hydrocarbon solvent such as hexane, heptane, cyclohexane, petroleum ether, benzene, toluene, xylene and the like; chlorinated hydrocarbons like chloroform, dichloro methane, ethylene dichloride; or mixtures thereof.

The reaction of 2-methyl-3-ethyl-4-oxo-4,5,6,7-tetrahydroindole (5) with morpholine and formaldehyde can be carried out in presence of solvent selected from alcohols like methanol, ethanol, butanol, propanol. The reaction can be carried out at a temperature of 25-30° C. to reflux temperature of the solvent over a period 30 minutes to 24 hours. The product molindone can be isolated by techniques known in art.

The compound molindone can be optionally converted into pharmaceutically acceptable salt. The salt can be selected from hydrochloride, hydro bromide, sulfuric, nitric, phosphoric, oxalic, tartaric, citric, acetic, succinic, maleic and the like. The salt formation can be carried out by techniques known in the art.

In the present invention, the compounds and intermediates can be isolated by techniques known in the art like filtration, concentration, crystallization, removal of solvent by evaporation, distillation, centrifugation, cooling etc.

The present invention is further illustrated by the following representative examples and does not limit the scope of the invention.

EXAMPLES

Example 1: Preparation of methyl 2-chloro-2-ethyl-3-oxobutanoate

A mixture of methyl acetoacetate (100 g), potassium tertiary butoxide (101.5 g) and tetrahydrofuran (400 ml) was stirred and a solution of ethyliodide (141 g) in tetrahydrofuran (200 ml) was added to it. The reaction mixture was stirred at 60° C. for about 15 hours. Water (250 ml) was added to the reaction mixture at 25° C. followed by addition of dichloromethane (500 ml). The organic layer was separated and concentrated. To the concentrate was added dichloromethane (1000 ml) and sulfuryl chloride (93.7 g) and the solution was stirred for about 18 hours at 25-30° C. Water (500 ml) was added to the reaction mixture. The organic layer was separated and concentrated to give the title compound.

Example 2: Preparation of 3-chloropentan-2-one

A mixture of methyl 2-chloro-2-ethyl-3-oxobutanoate (98.8 g) and water (240 ml) was treated with sulfuric acid (260 g) and stirred for 90 minutes at 75-80° C. The reaction mixture was poured into water (500 ml) and dichloromethane (500 ml). The organic layer was separated and concentrated. The concentrate was subjected to fractional distillation and pure compound was collected.

Example 3: Preparation of 3-chloropentan-2-one

A mixture of petane-2-one (15 g), acetic acid (60 ml) and N-chlorosuccinimide (24.4 g) was stirred for about 18 hours at 80-85° C. The reaction mixture was cooled and dichloromethane (100 ml) was added to it. The mixture was treated with sodium bicarbonate solution. The organic layer was separated and concentrated to give the title compound (2).

Example 4: Preparation of 2-(2-oxopentan-3-yl)cyclohexane-1,3-dione (4)

A mixture of 3-bromopentan-2-one (17 g), cyclohexane-1,3-dione (11.5 g), triethyl amine (15.6 g) and acetonitrile (100 ml)) was stirred for about 2 hours at 55-60° C. The reaction mixture was concentrated and ethyl acetate (170 ml) and water (85 ml) was added. The organic layer separated and concentrated. The residue was subjected to column chromatography (ethylacetate: cyclohexane). The title compound was obtained. $^1$H NMR (500 MHz, CDCl$_3$), δ 5.14 (S 1H), δ 4.37 (d 1H), δ 2.50-2.55 (m 2H) δ 2.35-2.38 (m 2H), δ 2.16 (s 3H), δ 2.00-2.05 (m 2H) δ 1.88-1.90 (m 2H), δ 1.00-1.02 (m 3H); $^{13}$C NMR (500 MHz, CDCl$_3$), 206.04, 199.34, 176.63, 103.70, 77.12, 36.62, 28.88, 25.44, 21.00, 16.55, 9.41 ppm; Dept135 NMR (500 MHz, CDCl$_3$): 103.70, 83.78, 36.62, 28.87, 28.65, 25.45, 24.69, 21.00, 9.41 ppm; Mass: [M+1]=197.

Example 5: Preparation of 2-methyl-3-ethyl-4-oxo-4,5,6,7-tetrahydroindole (5)

A mixture of 2-(2-oxopentan-3-yl)cyclohexane-1,3-dione (10 g), acetic acid (40 ml) and ammonium acetate (19.6 g) was stirred for about 3 hours at 95-100° C. The reaction mixture was cooled and concentrated. To the residue a mixture of ethyl acetate (60 ml) and water (50 ml) was added. The organic layer separated and concentrated to give the title compound.

Example 6: Preparation of 2-methyl-3-ethyl-4-oxo-4,5,6,7-tetrahydroindole (5)

A mixture of cyclohexane-1,3-dione (3 g), dimethyl sulfoxide (15 ml), triethyl amine (2.7 g) and 3-chloropentan-2-one (3.2 g) was stirred for about 24 hours at 40-45° C. Aqueous ammonia (15 ml) was added to the mixture and stirred for about 10 hours at 25-30° C. A mixture of water (60 ml) and ethyl acetate (30 ml) was added to it. The organic layer separated and concentrated. The residue was subjected to column chromatography (ethyl acetate/n-hexane). The title compound was obtained.

Example 7: Preparation of Molindone Hydrochloride

A mixture of 2-methyl-3-ethyl-4-oxo-4,5,6,7-tetrahydroindole (5 g), morpholine (4.42 g), paraformaldehyde (1.52 g) and ethanol (70 ml) was stirred for about 24 hours at 75-80° C. The reaction mixture was concentrated and water (50 ml) was added to the residue. The mixture was treated with concentrated hydrochloric acid followed by aqueous ammonia in presence of ethyl acetate. The organic layer was separated and concentrated to obtain molindone as a residue. Isopropanol hydrochloride was added to the residue and stirred for 30 minutes at 25-30° C. The solution was concentrated and ethyl acetate (15 ml) was added. The solid was filtered, washed with ethyl acetate and dried to obtain molindone hydrochloride.

The invention claimed is:

1. A process for the preparation of molindone (I) comprising:

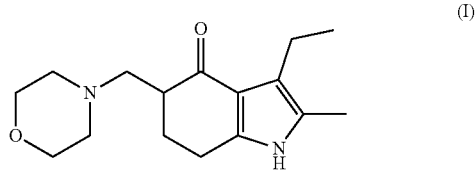 [SMILES: CCc1c(C)[nH]c2c1C(=O)C(CN1CCOCC1)CC2]

a) reacting compound (2) with cyclohexane-1,3-dione (3) to form 2-(2-oxopentan-3-yl)cyclohexane-1,3-dione (4)

(2)

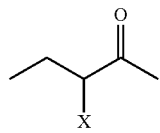

(3)

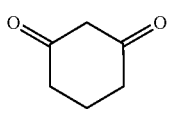

(4)

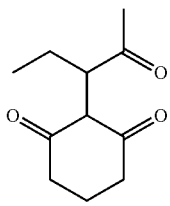

wherein X is Cl, Br or I, b) cyclizing 2-(2-oxopentan-3-yl)cyclohexane-1,3-dione (4) to 2-methyl-3-ethyl-4-oxo-4,5,6,7-tetrahydroindole (5), (5)

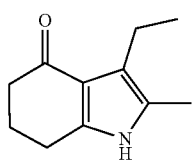

c) reacting 2-methyl-3-ethyl-4-oxo-4,5,6,7-tetrahydroindole (5) with morpholine and formaldehyde to give molindone (I), and d) optionally converting molindone (I) to its salt.

2. The process for preparation of compound (2) of as described in claim 1, comprising:

a) reacting compound (1') with ethyl halide and another halide source to form compound (2') wherein R is alkyl and X is Cl, Br or I, Compound (1')

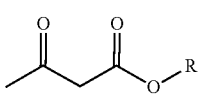

Compound (2')

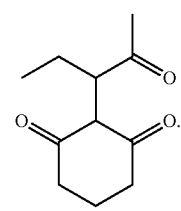

b) converting compound (2') to compound (2).

3. A compound, 2-(2-oxopentan-3-yl)cyclohexane-1,3-dione (4), (4)

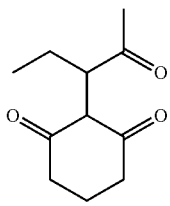

4. The process according to claim 1, wherein the cyclization process of step (b) is carried out in presence of reagent selected from ammonium acetate, aqueous ammonia, methanolic ammonia, ammonium chloride or urea and choline chloride.

5. The process according to claim 2, wherein ethyl halide is selected from ethyl iodide, ethyl bromide or ethyl chloride.

6. The process according to claim 2, wherein halide source is selected from N-chlorosuccimide, N-bromosuccinimde, N-Iodosuccinimide or sulfuryl chloride.

7. The process according to claim 2, wherein compound (2') is converted to compound (2) by treating with acid selected from hydrochloric acid, sulfuric acid, acetic acid or para toluene sulfonic acid.

8. The process according to claim 1, wherein molindone salt is hydrochloride salt.

9. The process according to claim 1, wherein the reaction of compound (2) and cyclohexane-1,3-dione (3) is carried out in presence of solvent and base.

10. The process according to claim 9, wherein the solvent is selected from acetonitrile, propionitrile, butyronitrile, ethyl acetate, ethyl acetoacetate, butyl acetate, propyl acetate, tetrahydrofuran, dioxane, dimethoxyethane, dimethyl ether, diisopropyl ether, diethyl ether, methyl tert-butyl ether, 1,2-dimethbxy ethane, dimethylformamide, toluene, dichloromethane or ethylene dichloride.

11. The process according to claim 9, wherein the base is selected from ethylamine, dimethylamine, diethylamine, dichloromethane, diisopropylethylamine, diisobutylamine, triethylamine, tributylamine, tert-Butylamine, pyridine or 4-dimethylaminopyridine.

* * * * *